United States Patent
Tomioka

(10) Patent No.: US 7,291,752 B2
(45) Date of Patent: Nov. 6, 2007

(54) PRODUCTION METHOD OF β-AMINO ACID

(75) Inventor: Kiyoshi Tomioka, Yokohama (JP)

(73) Assignee: Ajinomoto Co., Inc., Tokyo (JP)

( * ) Notice: Subject to any disclaimer, the term of this patent is extended or adjusted under 35 U.S.C. 154(b) by 645 days.

(21) Appl. No.: 10/765,832

(22) Filed: Jan. 29, 2004

(65) Prior Publication Data

US 2004/0210064 A1 Oct. 21, 2004

(30) Foreign Application Priority Data

Apr. 18, 2003 (JP) ............................ 2003-114593

(51) Int. Cl.
C07C 233/00 (2006.01)
(52) U.S. Cl. .................................... 564/169
(58) Field of Classification Search ................. 560/64; 564/169
See application file for complete search history.

(56) References Cited

U.S. PATENT DOCUMENTS 5,679,285 A * 10/1997 Bartmann et al. ..... 252/299.63

OTHER PUBLICATIONS

Hirohisa Doi, Takeo Sakai, Mayu Iguchi, Ken-ichi Yamada, and Kiyoshi Tomioka J.Am.Chem.Soc. 2003, 125,2886-2887.*
Derek C. Cole Tetrahedron vol. 50, No. 32, pp. 9517-9582, 1994.*
D. Cole, "Recent Stereoselective Synthetic Approaches to Beta-Amino Acids", Tetrahedron, vol. 50, No. 32, pp. 9517-9582, 1994.
G. Cardillo, et al., "Asymmetric Synthesis of Beta-Amino Acids and Alpha-Substituted Beta-Amino Acids", Chemical Socited Reviews, 1996, pp. 117-128.
M.P. Sibi, et al., "Chiral Lewis Acid Catalysis in Conjugate Additions of Oxygen-Benzylhydroxylamine to Unsaturated Amides. Enantioselective Synthesis of Beta-Amino Acid Precursors", J. Am. Chem. Soc., 1998, 120, pp. 6615-6616.
W. Zhuang, et al., "Catalytic Enantioselective Addition of Aromatic Amines to Enones: Synthesis of Optically Active Beta-Amino Acid Derivatives", Chem. Commun., 2001, pp. 1240-1241.
J. Myers, et al., "Asymmetric Synthesis of Beta-Amino Acid Derivatives Via Catalytic Conjugate Addition of Hydrazoic Acid to Unsaturated Imides", J. Am. Chem. Soc., 1999, 121, pp. 8959-8960.
G. Sundararajan, et al., "A New Polymer Anchored Chiral Catalyst for Asymmetric Michael Addition Reactions", Organic Letters, 2001, vol. 3, No. 3, pp. 389-392.
"External Chiral Ligand-Controlled Asymmetric Conjugate Addition of Lithium Amides to Alpha, Beta-Unsaturated Esters" (Report No. 29[P1]l-069), poster Mar. 27, 2003 (see Declaration Under 37 C.F.R. §1.132).
"External Chiral Ligand-Controlled Asymmetric Conjugate Addition of Lithium Amides to Alpha, Beta-Unsaturated Esters" (Report No. 29[P1]l-069), abstract, Mar. 5, 2003 (see Declaration Under 37 C.F.R. §1.132).
"External Chiral Ligand-Controlled Asymmetric Conjugate Addition of Lithium Amides to Alpha, Beta-Unsaturated Esters" (Report No. 29[P1]l-069), internet accessible Feb. 1, 2003 (see Declaration Under 37 C.F.R. §1.132).
H. Doi, et al., "Chiral Ligand-Controlled Asymmetric Conjugate Addition of Lithium Amides to Enoates", J. Am. Chem. Soc., 125 (10), pp. 2886-2887, 2003, Web Release Date: Feb. 12, 2003 (see Declaration Under 37 C.F.R. §1.132).
H. Doi, et al., "Chiral Ligand-Controlled Asymmetric Conjugate Addition of Lithium Amides to Enoates", J. Am. Chem. Soc., 125 (10), pp. 2886-2887, Mar. 12, 2003 (see Declaration Under 37 C.F.R. §1.132).

* cited by examiner

*Primary Examiner*—Johann R Richter
*Assistant Examiner*—Lalitha Nagubandi
(74) *Attorney, Agent, or Firm*—Oblon, Spivak, McClelland, Maier & Neustadt, P.C.

(57) ABSTRACT

A production method of an optically active β-amino acid represented by the formula (I)

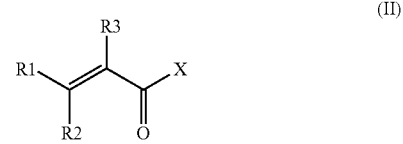

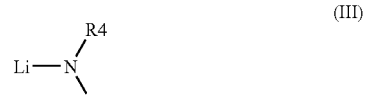

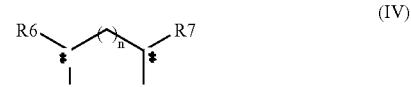

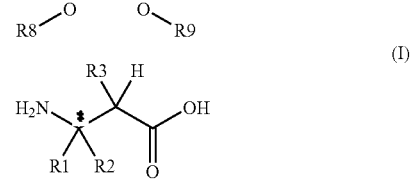

wherein each symbol is as defined in the specification, which includes reacting a compound represented by the formula (II) with a lithium amide represented by the formula (III) in the presence of a compound represented by the formula (IV).

22 Claims, No Drawings

PRODUCTION METHOD OF β-AMINO ACID

TECHNICAL FIELD OF THE INVENTION

The present invention relates to production methods of an optically active β-amino acid represented by the formula (I) to be mentioned later and an optically active compound represented by the formula (V) to be mentioned later, which is a precursor thereof. The optically active β-amino acid and a precursor thereof obtained by the present invention are useful as, for example, synthetic intermediates for β-lactam antibiotics.

BACKGROUND OF THE INVENTION

Synthesis methods of optically active β-amino acid have been introduced in, for example, Review and the like such as Tetrahedron, 1994, 50, 9517-9582, Chem. Soc. Rev., 1996, 117-128 and the like. Of these, an asymmetric 1,4-addition reaction of amine to α,β-unsaturated ester or amide (hereinafter sometimes to be abbreviated as α,β-unsaturated ester and the like) is a method attracting the highest attention because of the small number of reaction steps and easy availability of the starting materials. As a method for introducing asymmetry into the 1,4-addition reaction of amine to α,β-unsaturated ester and the like, there are three kinds of methods: i) a method using an optically active α,β-unsaturated ester or amide, ii) a method using an optically active amine and iii) a method using an asymmetric catalyst. Since the methods of i) and ii) are associated with difficulty in preparing an optically active form of a substrate, the development of the asymmetric catalytic method of iii) has been desired. The methods of iii) heretofore known include a method using alkoxyamine as an amine source (e.g., J. Am. Chem. Soc., 1998, 120, 6615-6616), a method using arylamine as an amine source (e.g., Chem. Commun. 2001, 1240-1241) and the like.

However, these methods have difficulty in finally leading to β-amino acid. In addition, the method using azide as an amine source (e.g., J. Am. Chem. Soc., 1999, 121, 8959-8960) has a problem in the safety of azide compound. Furthermore, a method wherein benzylamine, which is safe and easy to finally introduce into β-amino acid, is used as an amine source and an optically active β-amino acid is introduced by the asymmetric catalytic method has been reported in Org. Lett., 2001, 3, 389-392. This method, however, requires use of a polymer compound, which is not easy to prepare, as an asymmetric catalyst, and is not entirely satisfactory.

SUMMARY OF THE INVENTION

It is therefore an object of the present invention to provide a method for producing an optically active β-amino acid and a precursor thereof in good yields.

As a result of the intensive studies conducted by the present inventor in an attempt to achieve the above-mentioned object, it has been found that a 1,4-addition reaction of amine to α,β-unsaturated ester and the like proceeds in a high yield and a high asymmetric yield when a compound represented by the formula (IV) to be mentioned later (hereinafter sometimes to be abbreviated as compound (IV)) is used as an asymmetric catalyst and lithium amide represented by the formula (III) to be mentioned later (hereinafter sometimes to be abbreviated as compound (III)) is used as an amine source, which resulted in the completion of the present invention.

Accordingly, the present invention provides the following.

(1) a production method of an optically active β-amino acid represented by the formula (I)

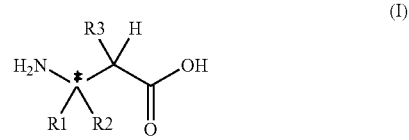

wherein
R1, R2 and R3
are each independently a hydrogen atom, or an optionally substituted alkyl, alkenyl or aryl group, or R1 and R3 may be linked to form a straight chain or branched chain alkylene having 1 to 4 carbon atoms, provided that R1 and R2 are not the same; and
* shows an asymmetric carbon,
(hereinafter sometimes to be abbreviated as optically active β-amino acid (I)), which comprises a step of reacting a compound represented by the formula (II)

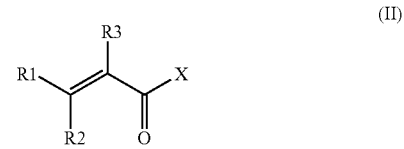

wherein R1, R2 and R3 are as defined above, and
X is an optionally substituted alkoxy, aryloxy, arylalkyloxy or amino group (hereinafter sometimes to be abbreviated as compound (II)), with a lithium amide represented by the formula (III)

wherein
R4 and R5 are the same or different and each is a silyl-protecting group, or an optionally substituted benzyl, benzhydryl or trityl group, provided that when one of R4 and R5 is a silyl-protecting group, then the other should be other than a silyl-protecting group, in the presence of a compound represented by the formula (IV)

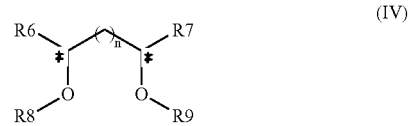

wherein
R6, R7, R8 and R9 are the same or different and each is an optionally substituted alkyl group or aryl group, or R6 and R7 may be linked to form a straight chain or branched chain alkylene having 2 to 5 carbon atoms, n is an integer of 0 to 3, and
* shows an asymmetric carbon that forms a configuration of (S,S) or (R,R),
(2) a production method of an optically active compound represented by the formula (V)

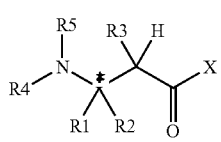

(V)

wherein
R1, R2 and R3 are each independently a hydrogen atom, or an optionally substituted alkyl, alkenyl or aryl group, or R1 and R3 may be linked to form a straight chain or branched chain alkylene having 1 to 4 carbon atoms, provided that R1 and R2 are not the same,
X is an optionally substituted alkoxy, aryloxy, arylalkyloxy or amino group,
R4 and R5 are the same or different and each is a silyl-protecting group or an optionally substituted benzyl, benzhydryl or trityl group, provided that when one of R4 and R5 is a silyl-protecting group, then the other should be other than a silyl-protecting group, and
* shows an asymmetric carbon,
which comprises reacting a compound represented by the formula (II)

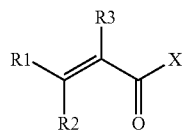

(II)

wherein R1, R2, R3 and X are as defined above, with a lithium amide represented by the formula (III)

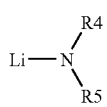

(III)

wherein R4 and R5 are as defined above, in the presence of a compound represented by the formula (IV)

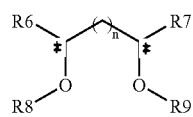

(IV)

wherein
R6, R7, R8 and R9 are the same or different and each is an optionally substituted alkyl or aryl group, or R6 and R7 may be linked to form a straight chain or branched chain alkylene having 2 to 5 carbon atoms,
n is an integer of 0 to 3, and
* shows an asymmetric carbon that forms a configuration of (S,S) or (R,R), (3) the production method of the above-mentioned (1) or (2), wherein the reaction is carried out in the additional presence of chlorotrimethylsilane,
(4) a production method of an optically active β-amino acid represented by the formula (I)

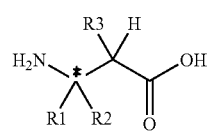

(I)

wherein
R1, R2 and R3 are each independently a hydrogen atom, or an optionally substituted alkyl, alkenyl or aryl group, or R1 and R3 may be linked to form a straight or branched chain alkylene having 1 to 4 carbon atoms, provided that R1 and R2 are not the same, and
*shows an asymmetric carbon,
which comprises subjecting a compound represented by the formula (V)

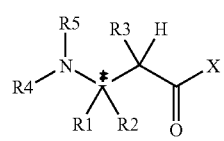

(V)

wherein
R1, R2, R3 and * are as defined above,
X is an optionally substituted alkoxy, aryloxy, arylalkyloxy or amino group, and
R4 and R5 are the same or different and each is a silyl-protecting group or an optionally substituted benzyl, benzhydryl or trityl group, provided that when one of R4 and R5 is a silyl-protecting group, then the other should be other than a silyl-protecting group,
to a deprotection reaction of an amino group and a carboxyl group,
(5) a production method of an optically active compound represented by the formula (VI)

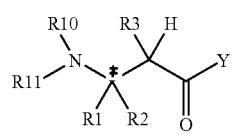

(VI)

wherein
R10 and R11 are the same or different and each is a hydrogen atom, or an optionally substituted benzyl, benzhydryl or trityl group, provided that when one of R10 and R11 is a hydrogen atom, then the other should be other than a hydrogen atom,
Y is a hydroxyl group, or an optionally substituted alkoxy, aryloxy, arylalkyloxy or amino group,
R1, R2 and R3 are each independently a hydrogen atom, or an optionally substituted alkyl, alkenyl or aryl group, or R1 and R3 may be linked to form a straight or branched chain alkylene having 1 to 4 carbon atoms, provided that R1 and R2 are not the same, and

* shows an asymmetric carbon (hereinafter sometimes to be abbreviated as optically active compound (VI)),
which comprises subjecting a compound represented by the formula (V)

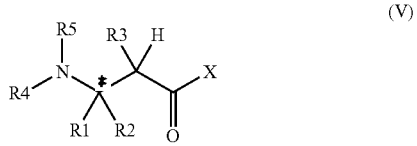

wherein
R1, R2, R3 and * are as defined above,
X is an optionally substituted alkoxy, aryloxy, arylalkyloxy or amino group, and
R4 and R5 are the same or different and each is a silyl-protecting group or an optionally substituted benzyl, benzhydryl or trityl group, provided that when one of R4 and R5 is a silyl-protecting group, then the other should be other than a silyl-protecting group,
to a quenching step,
(6) a production method of an optically active β-amino acid represented by the formula (I)

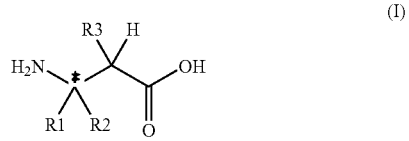

wherein
R1, R2 and R3 are each independently a hydrogen atom, or an optionally substituted alkyl, alkenyl or aryl group, or R1 and R3 may be linked to form a straight chain or branched chain alkylene having 1 to 4 carbon atoms, provided that R1 and R2 are not the same, and
* shows an asymmetric carbon,
which comprises subjecting a compound represented by the formula (VI)

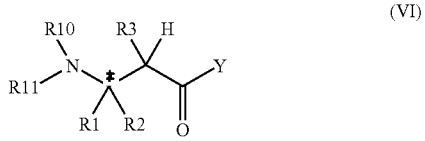

wherein R1, R2, R3 and * are as defined above,
R10 and R11 are the same or different and each is a hydrogen atom, or an optionally substituted benzyl, benzhydryl or trityl group, provided that when one of R10 and R11 is a hydrogen atom, then the other should be other than a hydrogen atom, and
Y is a hydroxyl group, or an optionally substituted alkoxy, aryloxy, arylalkyloxy or amino group,
to an amino-deprotecting reaction and, where necessary, a carboxyl-deprotecting reaction,
(7) the production method of any of the above-mentioned (1)-(6), wherein R2 is a hydrogen atom,
(8) the production method of any of the above-mentioned (1)-(7), wherein R2 and R3 are hydrogen atoms, R4 is a trimethylsilyl group, R5 is a benzyl group, R6 and R7 are phenyl groups, R8 and R9 are methyl groups, n is 0 and X is a tert-butoxy group, and
(9) the production method of the above-mentioned (8), wherein R1 is a phenyl group.

DETAILED DESCRIPTION OF THE INVENTION

Each symbol used in the present specification is explained in the following.

The alkyl group for R1, R2 and R3 is a straight chain or branched chain alkyl group preferably having 1-10, more preferably 1-4, carbon atoms, such as methyl group, ethyl group, n-propyl group, isopropyl group, n-butyl group, isobutyl group, sec-butyl group, tert-butyl group and the like, with preference given to methyl group and ethyl group.

The alkenyl group for R1, R2 and R3 is a straight chain or branched chain alkenyl group preferably having 2-10, more preferably 2-4, carbon atoms, such as ethenyl group, 1-propenyl group, 1-butenyl group and the like, with preference given to 1-propenyl group.

The aryl group for R1, R2 and R3 is an aryl group preferably having 6-20, more preferably 6-10, carbon atoms, such as phenyl group, naphthyl group and the like.

Each group for R1, R2 and R3 may be substituted by one or more substituents. As the substituent, for example, nitro group, straight chain or branched chain alkoxy group (number of carbon: 1-6, example: methoxy group), halogen atom (fluorine atom, chlorine atom, bromine atom, iodine atom) and the like can be mentioned.

The straight chain or branched chain alkylene having 1 to 4 carbon atoms, which may be formed by R1 and R3 in conjunction is, for example, methylene, ethylene, trimethylene, tetramethylene, methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene, 1-methyltetramethylene, 1,1-dimethyltetramethylene, 2-methyltetramethylene, 2,2-dimethyltetramethylene, 3-methyltetramethylene, 3,3-dimethyltetramethylene, 4-methyltetramethylene, 4,4-dimethyltetramethylene, 1-ethyltetramethylene, 2-ethyltetramethylene, 3-ethyltetramethylene, 4-ethyltetramethylene and the like, with preference given to trimethylene and tetramethylene.

The alkoxy group for X is a straight chain or branched chain alkoxy group preferably having 1-10, more preferably 1-4, carbon atoms, such as methoxy group, ethoxy group, n-propoxy group, isopropoxy group, n-butoxy group, isobutoxy group, tert-butoxy group and the like, with preference given to tert-butoxy group.

The aryloxy group for X is that wherein the aryl moiety is an aryl group preferably having 6-20, more preferably 6-10, carbon atoms, such as phenoxy group, naphthyloxy group and the like, with preference given to phenoxy group.

The arylalkyloxy group for X is that wherein the aryl moiety is an aryl group preferably having 6-20, more preferably 6-10, carbon atoms, and the alkyl moiety is a straight chain or branched chain alkyl group preferably having 1-6, more preferably 1-3, carbon atoms, such as benzyloxy group, phenethyloxy group, 3-phenylpropyloxy group and the like, with preference given to benzyloxy group.

The alkoxy group, aryloxy group and arylalkyloxy group for X may be substituted by one or more substituents. As the substituent here, for example, nitro group, straight chain or branched chain alkoxy group (number of carbon: 1-6, example: methoxy group), halogen atom (fluorine atom, chlorine atom, bromine atom, iodine atom) and the like can be mentioned.

The optionally substituted amino group for X is optionally substituted by 1 or 2 substituents shown in the following. In the case of di-substitution, each substituent may be the same or different. As the substituent here, a straight chain or branched chain alkyl group (number of carbon: 1-4, example: methyl, ethyl, isopropyl), an acyl group (example: formyl, acetyl, propionyl, benzoyl etc.) and the like can be mentioned. Specifically, amino, dimethylamino, diethylamino, formylamino, acetylamino, benzoylamino and the like can be mentioned. The amino group may form cyclic amine or amide or urethane having 1 or 2 atoms from an oxygen atom, a sulfur atom and a nitrogen atom in the ring. For example, pyrrolidine, morpholine, thiomorpholine, optionally substituted oxazolidinone and the like can be mentioned.

The silyl-protecting group for R4 and R5 is a substituted silyl group that acts as an amino-protecting group, which is substituted by 2 or 3, the same or different substituents mentioned below. The substituents here include a straight chain or branched chain alkyl group (number of carbon: 1-4, example: methyl, ethyl, tert-butyl) and an aryl group (number of carbon: 6-10, example: phenyl). Concrete examples of the silyl-protecting group include trimethylsilyl group, triphenylsilyl group, tert-butyldimethylsilyl group, tert-butyldiphenylsilyl group, dimethylsilyl group, diphenylsilyl group and the like, with preference given to trimethylsilyl group.

In the optionally substituted benzyl group, benzhydryl group and trityl group for R4 and R5, the benzene ring of benzyl group, benzhydryl group and trityl group may be substituted by one or more substituents mentioned below. As the substituent here, for example, a nitro group, a straight chain or branched chain alkoxy group (number of carbon: 1-6, example: methoxy group), a halogen atom (fluorine atom, chlorine atom, bromine atom, iodine atom) and the like can be mentioned, with preference given to benzyl group.

The alkyl group for R6, R7, R8 and R9 is a straight chain or branched chain alkyl group preferably having 1-10, more preferably 1-4, carbon atoms, such as methyl group, ethyl group, n-propyl group, isopropyl group, n-butyl group, isobutyl group, sec-butyl group, tert-butyl group and the like, with preference given to methyl group.

The aryl group for R6, R7, R8 and R9 is an aryl group preferably having 6-20, more preferably 6-10, carbon atoms, such as phenyl group, naphthyl group and the like.

The alkyl group and aryl group for R6, R7, R8 and R9 may be substituted by one or more substituents mentioned below. As the substituent here, for example, a nitro group, a straight chain or branched chain alkoxy group (number of carbon: 1-6, example: methoxy group), a halogen atom (fluorine atom, chlorine atom, bromine atom, iodine atom) and the like can be mentioned.

The straight chain or branched chain alkylene having 2 to 5 carbon atoms, that may be formed by R6 and R7 in conjunction, is, for example, ethylene, trimethylene, tetramethylene, pentamethylene, 1-methylethylene, 2-methylethylene, 1,1-dimethylethylene, 2,2-dimethylethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene, 1-methyltetramethylene, 1,1-dimethyltetramethylene, 2-methyltetramethylene, 2,2-dimethyltetramethylene, 3-methyltetramethylene, 3,3-dimethyltetramethylene, 4-methyltetramethylene, 4,4-dimethyltetramethylene, 1-ethyltetramethylene, 2-ethyltetramethylene, 3-ethyltetramethylene, 4-ethyltetramethylene, 1-methylpentamethylene, 1,1-dimethylpentamethylene and the like, with preference given to tetramethylene.

The optionally substituted benzyl group, benzhydryl group or trityl group for R10 and R11 is the same as the optionally substituted benzyl group, benzhydryl group or trityl group for R4 and R5, and the optionally substituted alkoxy group, aryloxy group, arylalkyloxy group or amino group for Y is the same as the optionally substituted alkoxy group, aryloxy group, arylalkyloxy group or amino group for X.

The production methods of the optically active compound (V) and optically active β-amino acid (I) of the present invention are described in the following.

The optically active compound (V) of the present invention can be produced by reacting compound (II) with compound (III) in the presence of compound (IV), and by deprotection of compound (V), an optically active β-amino acid (I) can be produced.

The compounds (II), (III) and (IV) are known compounds that can be produced easily or can be prepared by a conventional method.

The compound (III) may be prepared before use for the reaction, or produced in the reaction system by, for example, adding alkyllithium such as n-butyllithium and the like and mine to the reaction system.

The amount of compound (III) to be used is generally in he range of 1-8 molar equivalents, and preferably 1-4 molar equivalents, relative to compound (II) in view of the yield and economic aspect.

The amount of compound (IV) to be used is generally 0.05-8 molar equivalents, and preferably 0.1-4 molar equivalents, relative to compound (II), in view of the yield and economic aspect.

This reaction is generally carried out in the presence of a solvent. The solvent is not particularly limited as long as it does not exert an adverse influence on the reaction, and may be, for example, aliphatic hydrocarbons such as pentane, hexane, heptane, cyclohexane, methylcyclohexane and the like; aromatic hydrocarbons such as benzene, toluene, xylene and the like; ethers such as diethyl ether, diisopropyl ether, tert-butylmethyl ether, tetrahydrofuran, dioxane and the like, halogenated hydrocarbons such as methylene chloride, chloroform, 1,2-dichloroethane and the like; nitrites such as acetonitrile, benzonitrile and the like; nitrogen-containing aromatic ring compounds such as pyridine and the like; amides such as dimethylformamide, N-methylpyrrolidone, N,N'-dimethylimidazolidinone, hexamethylphosphoric triamide and the like; and the like. Of these, aromatic hydrocarbon and halogenated hydrocarbon are preferable from the aspects of the yield and asymmetric yield, particularly preferably toluene. The amount of the solvent to be used is preferably in the range of 2 to 60-fold amount, more preferably 6 to 30-fold amount, relative to compound (II) in weight ratio, from the aspects of the yield and asymmetric yield.

While the reaction temperature varies depending on the kinds of compound (II) and compound (III), the kind of the solvent to be used and the like, it is generally −90° C. to −20° C., preferably −80° C. to −60° C.

While the reaction time varies depending on the reaction temperature and the like, it is generally 0.1 to 5 hr, preferably 0.2 to 3 hr.

This reaction is preferably carried out in the additional presence of chlorotrimethylsilane. Addition of chlorotrimethylsilane improves the reaction efficiency of compound (II) and compound (III), thereby increasing the yield of optically active compound (V). When chlorotrimethylsilane is added, the amount of addition thereof is preferably in the range of 1-10 molar equivalents, more preferably 3-6 molar equivalents, relative to compound (II), in view of the yield and economic aspect.

The reaction is preferably carried out under an inert gas atmosphere of argon, helium, nitrogen and the like.

While the method of operation is not particularly limited, the reaction is carried out by, for example, a method comprising adding a solution of compound (II) in a solvent to a solution of compound (III) and compound (IV) in a solvent under an inert gas atmosphere of argon, helium, nitrogen and the like, and the like. When chlorotrimethylsilane is to be added, it can be dissolved in a solvent together with compound (II).

When the reaction step is to be stopped, a quenching agent is generally added to the reaction solution. As the quenching agent, acidic aqueous solutions such as an aqueous ammonium chloride solution, an aqueous hydrochloric acid solution and the like, alkaline aqueous solutions such as an aqueous sodium hydrogen carbonate solution, an aqueous sodium carbonate solution, an aqueous sodium hydroxide solution and the like, and the like can be mentioned.

Isolation and purification from a reaction mixture containing optically active compound (V) can be conducted according to a method generally used for isolation and purification of organic compounds, such as extraction, column chromatography, crystallization and the like. When optically active compound (V) is to be successively introduced into optically active β-amino acid (I), it is not generally necessary to isolate or purify optically active compound (V), and the reaction solution can be used for the next step as it is or after concentration, substitution and the like of the solvent as necessary.

The obtained optically active compound (V) can be introduced into optically active β-amino acid (I) by deprotection reaction of amino group (conversion of R4 and R5 into hydrogen atom) and deprotection reaction of carboxyl group (conversion of X into hydroxyl group). The conditions of these deprotection reactions are not particularly limited, and a method well known to those of ordinary skill in the art can be used. For example, when amino group is protected by benzyl group, benzhydryl group or trityl group, it can be deprotected by hydrogenation reaction in the presence of a catalyst such as a palladium catalyst and the like. When amino group is protected by silyl-protecting group, it can be deprotected by hydrolysis in an acidic aqueous solution or alkaline aqueous solution. In addition, alkoxy group, aryloxy group, arylalkyloxy group and amino group, which are carboxyl-protecting groups, can be also deprotected by hydrolysis in an acidic aqueous solution or alkaline aqueous solution. The silyl-protecting group tends to be deprotected relatively easily as compared to the protecting group of these carboxyl groups. When, as mentioned above, the reaction is quenched by adding an acidic aqueous solution or alkaline aqueous solution to a reaction solution containing optically active compound (V), the silyl-protecting group is generally deprotected at this point by hydrolysis reaction, thereby affording an optically active compound of the formula (V) wherein one of R4 and R5 is hydrogen atom. The carboxyl-protecting group is sometimes also deprotected by hydrolysis reaction in the aforementioned quenching step, thereby affording an optically active compound of the formula (V) wherein X is hydroxyl group. When the aforementioned quenching step is performed, therefore, the quenching step may become a part of the deprotection step of optically active compound (V). In other words, after the completion of the above-mentioned quenching step, optically active compound (V) becomes an optically active compound represented by the following formula (VI)

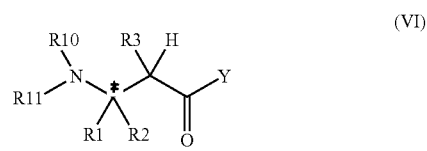

wherein R10 and R11 are the same or different and each is a hydrogen atom, or an optionally substituted benzyl, benzhydryl or trityl group, provided that when one of R10 and R11 is a hydrogen atom, the other is other than a hydrogen atom, Y is a hydroxyl group, or an optionally substituted alkoxy, aryloxy, arylalkyloxy or amino group, and R1, R2, R3 and * are as defined above.

For explanation of the deprotection step through a concrete example, in the case of, for example, optically active compound (V) wherein R4 and R5 are trimethylsilyl group and benzyl group and X is a tert-butoxy group, the trimethylsilyl group is deprotected by a quenching step, and then hydrogenation reaction is carried out in the presence of a palladium catalyst such as a Pearlman's catalyst and the like, whereby the benzyl group is deprotected (see Example 1 below).

Furthermore, trifluoroacetic acid is reacted to remove tert-butoxy group. In this case, the obtained optically active β-amino acid (I) becomes trifluoroacetic acid salt, which may be desalted by ion exchange resin as necessary. More specifically, for example, Tetrahedron 1994, 50, 3975-3986 discloses an example of tert-butyl (2S,3S)-3-amino-2-hydroxy-4-phenylbutanoate, wherein trifluoroacetic acid is added, the mixture is stirred at room temperature for about 14 hr, the solvent is evaporated under reduced pressure, the residue is dissolved in aqueous hydrochloric acid solution, the solution is treated with an ion exchange resin (Dowex 50X8-200), and the effluent is concentrated to give the object optically active β-amino acid. Depending on the kind of β-amino acid, desalting can be performed by neutral crystallization by appropriately adjusting the pH of the aqueous solution without using an ion exchange resin, as in the case of α-amino acid.

The present invention is described in more detail in the following by means of Examples, which are not to be construed as limitative.

The measurement conditions are shown in the following.

$^1$H-NMR (500 MHz) and $^{13}$C-NMR (125 MHz) were measured in CDCl$_3$. The chemical shift is expressed in ppm from internal standard tetramethylsilane to the downfield.

The asymmetric yield (% ee) was determined by HPLC analysis using an optically active column.

STARTING MATERIAL SYNTHETIC EXAMPLE 1 tert-butyl 3-(2-naphthyl)-2-propenoate

To a suspension of tert-butyl triphenylphosphoranediylacetate (8.82 g, 23.4 mmol) in toluene (15 mL) was added a solution of 2-naphthaldehyde (2.82 g, 18.0 mmol) in toluene (15 mL). The mixture was stirred at room temperature for 18 hr and filtered. The filtrate was concentrated, subjected to silica gel column chromatography (ethyl acetate/hexane=1/30) and recrystallized (acetonitrile/water=1/2) to give the title compound as a colorless paste (4.1 g, yield 91%), melting point: 74-75° C.

$^1$H-NMR (500 MHz, CDCl$_3$)δ: 1.57(9H, s), 6.49(1H, d, J=15.9 Hz), 7.49-7.51(2H, m), 7.66(1H, d, J=8.3 Hz), 7.75 (1H, d, J=15.9 Hz), 7.81-7.86(3H, m), 7.91(1H, S). $^{13}$C-NMR(125 MHz, CDCl$_3$)δ: 28.2, 80.5, 120.4, 123.6, 126.6, 127.1, 127.8, 128.5, 128.6, 129.6, 132.2, 133.3, 134.1, 143.6, 166.4. IR(nujol): 1713, 1150 cm$^{-1}$. EIMS m/z: 254 (M$^+$). C$_{17}$H$_{18}$O$_2$: Calculated: C, 80.28; H, 7.13. Found: C, 80.5; H, 7.13.

EXAMPLE 1

(1) tert-butyl 3-(benzylamino)-3-phenylpropanoate

Under an argon atmosphere, n-butyllithium (0.9 mL, 1.6 M in hexane solution, 1.5 mmol) was added to a solution of N-benzyltrimethylsilylamine (0.3 mL, 1.5 mmol) in toluene (4 mL) at −78° C. over 5 min. After stirring for 0.5 hr, a solution of (1R,2R)-1,2-dimethoxy-1,2-diphenylethane (436 mg, 1.8 mmol) in toluene (2 mL) was added, and the mixture was stirred at −78° C. for 0.5 hr. Thereto was added a solution of tert-butyl cinnamate (204 mg, 1.0 mmol) and chlorotrimethylsilane (0.63 mL, 5.0 mmol) in toluene (2 mL) over 5 min. The mixture was stirred at −78° C. for 5 hr, and quenched with saturated aqueous ammonium chloride solution (1.5 mL). After adding a saturated aqueous sodium hydrogen carbonate solution (20 mL), the mixture was extracted with ethyl acetate. The organic layer was washed with brine and dried over sodium sulfate, after which it was concentrated and subjected to silica gel column chromatography (ethyl acetate/hexane=1/25) to give the title compound (302 mg, yield 97%) as a colorless oil of [α]$^{25}_D$+32.5 (c 1.35, CHCl$_3$).

97% ee (HPLC, Daicel Chiralpak OD-H, hexane/isopropanol=100/1, 1.0 mL/min, 254 nm, major 5.7 min and minor 6.7 min). $^1$H-NMR (500 MHz, CDCl$_3$)δ: 1.37(9H, s), 2.11 (1H, brs), 2.53(1H, dd, J=5.2, 15.3 Hz), 2.64(1H, dd, J=8.9, 15.3 Hz), 3.54 and 3.64(each 1H, d, J=13.1 Hz), 4.07(1H, dd, J=5.2, 8.9 Hz), 7.21-7.37(10H, m). $^{13}$C-NMR (125 MHz, CDCl$_3$)δ: 28.0, 44.3, 51.4, 59.2, 80.6, 126.8, 127.25, 127.34, 128.1, 128.3, 128.5, 140.4, 142.7, 171.1. IR (neat): 3333, 1724, 1150 cm$^{-1}$. EIMS m/z: 311(M$^+$), 254(M-t-Bu), 220 (M-Bn), 196(M-CO$_2$t-Bu), 164(256-Bn)

These are identical to those reported in Bull, S. D.; Davies, S. G.; Fenton, G.; Mulvaney, A. W.; Prasad, R. S.; and Smith, A. D. J. Chem. Soc. Perkin Trans. 1, 2000, 3765-3774.

(2) tert-butyl (R)-3-amino-3-phenylpropionate

A mixture of tert-butyl 3-(benzylamino)-3-phenylpropanoate (115 mg, 0.37 mmol) obtained in (1) and Pearlman's catalyst (30.8 mg, 0.074 mmol) in methanol (1.5 mL) was stirred at room temperature under a hydrogen atmosphere (7 atm). The reaction mixture was filtered and concentrated. Purification by silica gel column chromatography (ethyl acetate/hexane=1/2) gave the title compound (77 mg, 94%) as a colorless oil of [α]$^{25}_D$+18.8 (c 0.75, CHCl$_3$). $^1$H-NMR (500 MHz, CDCl$_3$)δ: 1.42(9H, s), 1.89(2H, brs), 2.59(2H, d, J=6.8 Hz), 4.38(1H, t, J=6.8 Hz), 7.23-7.37(5H, m). $^{13}$C-NMR (125 MHz, CDCl$_3$)δ: 28.0, 45.3, 52.7, 80.7, 126.3, 127.3, 128.5, 144.7, 171.3. IR (neat): 3383, 2978, 1724, 1150 cm$^{-1}$. EIMS m/z: 221(M$^+$), 164(M-t-Bu), 106(M-CO$_2$t-Bu).

These are identical to those reported in Davies, S. G.; Garrido, N. M.; Ichihara, O.; and Walters, I. A. S. J. Chem. Soc., Perkin Trans. 1, 1993, 1153-1155.

EXAMPLE 2 tert-butyl 3-(dibenzylamino)-3-phenylpropanoate

Under an argon atmosphere, n-butyllithium (0.9 mL, 1.6 M in hexane solution, 1.5 mmol) was added to a solution of N-benzyltrimethylsilylamine (0.3 mL, 1.5 mmol) in toluene (4 mL) at −78° C. over 5 min. After stirring for 0.5 hr, a solution of (1R,2R)-1,2-dimethoxy-1,2-diphenylethane (872 mg, 3.6 mmol) in toluene (2 mL) was added and the mixture was stirred. Thereto was added a solution of tert-butyl cinnamate (204 mg, 1.0 mmol) and chlorotrimethylsilane (0.63 mL, 5.0 mmol) in toluene (2 mL) over 5 min. The mixture was stirred at −20° C. for 0.2 hr, and quenched with a saturated aqueous ammonium chloride solution (1.5 mL). After adding a saturated aqueous sodium hydrogen carbonate solution (20 mL), the mixture was extracted with ethyl acetate. The organic layer was washed with brine and dried over sodium sulfate, after which it was concentrated and purified by silica gel column chromatography (ethyl acetate/hexane=1/70) to give the title compound as a colorless oil (193 mg, yield 48%).

4% ee (HPLC, Daicel Chiralpak OD-H, hexane/isopropanol=250/1, 1.0 mL/min, 254 nm, major 10.6 min and minor 7.7 min). $^1$H-NMR (500 MHz, CDCl$_3$)δ: 1.33(9H, s), 2.71(1H, dd, J=8.7, 14.5 Hz), 2.99(1H, dd, J=6.9, 14.5 Hz), 3.28(1H, d, J=13.8 Hz), 3.71(1H, d, J=13.8 Hz), 4.27(1H, dd, J=6.9, 8.7 Hz), 7.20-7.36(15H, m). $^{13}$C-NMR (125 MHz, CDCl$_3$)δ: 27.9, 37.3, 53.9, 59.2, 80.4, 126.9, 127.2, 127.9, 128.1, 128.7, 128.8, 138.3, 139.8, 171.0. IR (neat): 3425, 1728, 1153 cm$^{-1}$. EIMS m/z: 401(M$^+$), 344(M-t-Bu), 310 (M-Bn), 286(M-CO$_2$t-Bu).

These are identical to those reported in Bull, S. D.; Davies, S. G.; Fenton, G.; Mulvaney, A. W.; Prasad, R. S.; and Smith, A. D. J. Chem. Soc. Perkin Trans. 1, 2000, 3765-3774.

EXAMPLE 3 tert-butyl 3-(benzylamino)butanoate

Synthesis in the same manner as in Example 1(1) using tert-butyl trans-2-butenoate instead of tert-butyl cinnamate and purification by silica gel column chromatography (ethyl acetate/hexane=1/10) gave the title compound (229 mg, yield 92%) as a colorless oil of [α]$^{25}_D$+13.8 (c 1.03, CHCl$_3$).

97% ee (HPLC, Daicel Chiralpak OD-H, hexane/isopropanol=400/1, 1.0.mL/min, 254 nm, major 21.8 min and minor 19.0 min). $^1$H-NMR (500 MHz, CDCl$_3$)δ: 1.14(3H, d, J=6.1 Hz), 1.44(9H, s), 1.72(1H, brs), 2.29(1H, dd, J=5.8, 15.0 Hz), 2.41(1H, dd, J=7.0, 15.0 Hz), 3.12(1H, ddq, J=5.8, 6.1, 7.0 Hz), 3.75 and 3.82(each 1H, d, J=12.8 Hz), 7.22-7.33(5H, m). $^{13}$C-NMR (125 MHz, CDCl$_3$)δ: 20.4, 28.1, 42.8, 49.9, 51.2, 80.3, 126.8, 128.1, 128.3, 140.5, 171.7. IR (neat): 3329, 1724, 1157 cm$^{-1}$. EIMS m/z: 249(M$^+$), 192 (M-t-Bu), 134(M-CO$_2$t-Bu). C$_{15}$H$_{23}$NO$_2$: Calculated: C, 72.25; H, 9.30; N, 5.62. Found: C, 72.47; H, 9.12; N, 5.39.

EXAMPLE 4 tert-butyl 3-(benzylamino)-4-methylpentanoate

Synthesis in the same manner as in Example 1(1) using tert-butyl trans-4-methyl-2-pentenoate instead of tert-butyl cinnamate and purification by silica gel column chromatography (ethyl acetate/hexane=1/30) gave the title compound (194 mg, yield 70%) as a colorless oil of $[\alpha]^{25}_D$+6.33 (c 1.09, CHCl$_3$).

99% ee (HPLC, Daicel Chiralpak OJ, hexane/isopropanol=1000/1, 0.5 mL/min, 254 nm, major 13.4 min and minor 16.3 min). $^1$H-NMR (500 MHz, CDCl$_3$)δ: 0.90 and 0.92(each 3H, d, J=7.1 Hz), 1.44(9H, s), 1.51(1H, brs), 1.88(1H, dq, J=7.1, 8.7 Hz), 2.26(1H, dd, J=8.2, 15.0 Hz), 2.36(1H, dd, J=4.6, 15.0 Hz), 2.86(1H, ddd, J=4.6, 8.2, 8.7 Hz), 3.76 and 3.79(each 1H, d, J=12.8 Hz), 7.21-7.35(5H, m). $^{13}$C-NMR (125 MHz, CDCl$_3$)δ: 17.6, 18.8, 28.1, 30.4, 37.4, 51.6, 59.9, 80.3, 126.8, 128.1, 128.2, 140.9, 172.5. IR (neat): 3352, 1728, 1153 cm$^{-1}$. EIMS m/z: 278(M$^+$), 234 (M-i-PrH), 221(M-t-Bu), 162(M-CO$_2$t-Bu). C$_{17}$H$_{27}$NO$_2$: Calculated: C, 73.61; H, 9.81; N, 5.05. Found: C, 73.42; H, 9.51; N, 5.04.

EXAMPLE 5 tert-butyl 3-(benzylamino)-4-hexenoate

Synthesis in the same manner as in Example 1(1) using tert-butyl (2E,4E)-2,4-hexadienoate instead of tert-butyl cinnamate and purification by silica gel column chromatography (ethyl acetate/hexane=1/20) gave the title compound (201 mg, yield 73%) as a colorless oil of $[\alpha]^{25}_D$+13.0 (c 1.01, CHCl$_3$).

98% ee (HPLC, Daicel Chiralpak OB-H, hexane/isopropanol=1000/1, 1.0 mL/min, 254 nm, major 7.6 min and minor 9.0 min). $^1$H-NMR (500 MHz, CDCl$_3$)δ: 1.42(9H, s), 1.70(3H, d, J=6.4 Hz), 2.35(1H, dd, J=6.4, 14.8 Hz), 2.44 (1H, dd, J=7.7, 14.8 Hz), 3.43(1H, ddd, J=6.4, 7.6, 7.7 Hz), 3.80 and 3.64(each 1H, d, J=13.2 Hz), 5.32(1H, dd, J=7.6, 15.3 Hz), 5.61(1H, dq, J=6.4, 15.3 Hz), 7.21-7.31(5H, m). $^{13}$C-NMR (125 MHz, CDCl$_3$)δ: 17.7, 28.1, 42.3, 51.2, 57.2, 80.5, 126.8, 127.7, 128.2, 128.3, 132.5, 140.5, 171.3. IR (neat): 3329, 1728, 1157 cm$^{-1}$. EIMS m/z: 275(M$^+$), 218 (M-t-Bu), 184(M-Bn), 160(M-CO$_2$t-Bu). C$_{17}$H$_{25}$NO$_2$: Calculated: C, 74.14; H, 9.15; N, 5.09. Found: C, 74.36; H, 9.33; N, 5.22.

EXAMPLE 6 tert-butyl 3-(benzylamino)-3-(1-naphthyl)propanoate

Synthesis in the same manner as in Example 1(1) using tert-butyl trans-3-(1-naphthyl)-2-propenoate instead of tert-butyl cinnamate and purification by silica gel column chromatography (ether/hexane=1/15) gave the title compound (358 mg, yield 99%) as a colorless oil of $[\alpha]^{25}_D$+4.9 (c 0.94, CHCl$_3$).

91% ee (HPLC, Daicel Chiralpak OD-H, hexane/isopropanol=100/1, 1.0 mL/min, 254 nm, major 9.5 min and minor 14.3 min). $^1$H-NMR (500 MHz, CDCl$_3$)δ: 1.37(9H, s), 2.04(1H, brs), 2.67-2.75(2H, m), 3.62 and 3.72(each 1H, d, J=13.1 Hz), 4.97(1H, dd, J=4.9, 8.3 Hz), 7.22-7.29(5H, m), 7.41-7.52(3H, m), 7.74-7.79(2H, m), 7.81-7.89(1H, m), 8.23 (1H, d, J=7.4 Hz). $^{13}$C-NMR (125 MHz, CDCl$_3$)δ: 28.0, 43.7, 51.6, 80.8, 123.0, 123.9, 125.4, 125.6, 126.0, 126.9, 127.7, 128.2, 128.3, 128.9, 131.4, 134.0, 138.1, 140.4, 171.4. IR (neat): 3333, 1724, 1150 cm$^{-1}$. EIMS m/z: 361 (M$^+$), 304(M-t-Bu), 270(M-Bn), 246(M-CO$_2$t-Bu). C$_{24}$H$_{27}$NO$_2$: Calculated: C, 79.74; H, 7.53; N, 3.87. Found: C, 79.76; H, 7.59; N, 3.69.

EXAMPLE 7 tert-butyl 3-(benzylamino)-3-(2-naphthyl)propanoate

Synthesis in the same manner as in Example 1(1) using tert-butyl trans-3-(2-naphthyl)-2-propenoate instead of tert-butyl cinnamate and purification by silica gel column chromatography (ether/hexane=1/10) gave the title compound (325 mg, yield 90%) as a colorless oil of $[\alpha]^{25}_D$+35.5 (c 1.10, CHCl$_3$).

94% ee (HPLC, Daicel Chiralpak OD-H, hexane/isopropanol=100/1, 1.0 mL/min, 254 nm, major 8.1 min and minor 9.6 min). $^1$H-NMR (500 MHz, CDCl$_3$)δ: 1.36(9H, s), 2.01 (1H, brs), 2.61(1H, dd, J=5.2, 15.3 Hz), 2.72(1H, dd, J=8.9, 15.3 Hz), 3.58 and 3.66(each 1H, d, J=13.1 Hz), 4.25(1H, dd, J=5.2, 8.9 Hz), 7.22-7.32 (5H, m), 7.45-7.54(3H, m), 7.79-7.86(4H, m). $^{13}$C-NMR (125 MHz, CDCl$_3$)δ: 28.0, 44.2, 51.4, 59.3, 80.7, 125.0, 125.7, 126.0, 126.3, 126.9, 127.7, 127.8, 128.2, 128.3, 128.4, 133.0, 133.4, 140.1, 140.3, 171.1. IR (neat): 3333, 1724, 1150 cm$^{-1}$. EIMS m/z: 361(M$^+$), 304(M-t-Bu), 270(M-Bn), 246(M-CO$_2$t-Bu). C$_{24}$H$_{27}$NO$_2$: Calculated: C, 79.74; H, 7.53; N, 3.87. Found: C, 79.49; H, 7.52; N, 3.88.

EXAMPLE 8

(1) tert-butyl (1R,2S)-2-(benzylamino)cyclopentanecarboxylate (cis Form)

Synthesis in the same manner as in Example 1(1) using tert-butyl 1-cyclopentenecarboxylate instead of tert-butyl cinnamate and purification by silica gel column chromatography (ethyl acetate/hexane=1/20) gave the title compound (168 mg, yield 61%) as a colorless oil of $[\alpha]^{25}_D$−29.4 (c 1.18, CHCl$_3$).

92% ee (HPLC, Daicel Chiralpak OD-H, hexane/isopropanol=400/1, 1.0 mL/min, 254 nm, major 11.3 min and minor 9.7 min). $^1$H-NMR (500 MHz, CDCl$_3$)δ: 1.45(9H, s), 1.51-2.01(6H, m), 1.74(1H, brs), 2.84(1H, m), 3.27(1H, m), 3.80(2H, s), 7.21-7.33(5H, m). $^{13}$C-NMR (125 MHz, CDCl$_3$)δ: 22.1, 27.5, 28.2, 31.6, 48.3, 52.3, 61.4, 80.1, 126.7, 128.0, 128.3, 140.7, 174.0. IR (neat): 3337, 1720, 1150 cm$^{-1}$. EIMS m/z: 275(M$^+$), 218(M-t-Bu), 184(M-Bn). C$_{17}$H$_{25}$NO$_2$: Calculated: C, 74.14; H, 9.15; N, 5.09. Found: C, 73.86; H, 9.33; N, 4.98.

(2) tert-butyl (1R,2S)-2-aminocyclopentanecarboxylate tert-Butyl (1R,2S)-2-(benzylamino)cyclopentanecarboxylate (cis form) obtained in (1) was debenzylated according to the method similar to that in Example 1(2) and purified by silica gel column chromatography (methanol/ether=1/2) to give the title compound (143 mg, yield 77%) as a colorless oil of $[\alpha]^{25}_D$−4.0 (c 1.0, CHCl$_3$).

$^1$H-NMR (500 MHz, CDCl$_3$)δ: 1.47(9H, s), 1.49-1.60 (4H, m), 1.79-2.02(4H, m), 2.67-2.72(1H, m), 3.54-3.58(1H, m). $^{13}$C-NMR (125 MHz, CDCl$_3$)δ: 22.3, 26.2, 28.2, 34.8, 51.1, 54.9, 80.3, 173.6. IR (neat): 3383, 1724, 1366, 1153 cm$^{-1}$. EIMS m/z: 185(M$^+$), 128(M-t-Bu), 84(M-CO$_2$ t-Bu).

These are identical to those reported in Davies, S. G.; Ichihara, O.; Lenoir, I.; Walters, I. A. S. J. Chem. Soc., Perkin Trans. 1, 1994, 1141-1145.

EXAMPLE 9 tert-butyl (1S,2S)-2-(benzylamino)cyclopentanecarboxylate (trans Form)

The product obtained by the synthesis in Example 8(1) was purified by silica gel column chromatography (ethyl acetate/hexane=1/2) to give the title compound (25 mg, yield 9%) as a colorless oil of [α]$^{25}_D$+49.8 (c 0.51, CHCl$_3$) 97% ee (HPLC, Daicel Chiralpak OD-H, hexane/isopropanol=100/1, 1.0 mL/min, 254 nm, major 7.3 min and minor 6.2 min). $^1$H-NMR (500 MHz, CDCl$_3$)δ: 1.43(9H, s), 1.61-2.05(6H, m), 2.05(1H, brs), 2.52(1H, m), 3.26(1H, m), 3.75 and 3.82(each 1H, d, J=13.1 Hz), 7.24-7.32(5H, m). $^{13}$C-NMR (125 MHz, CDCl$_3$)δ: 23.5, 28.1, 28.5, 33.1, 51.8, 52.5, 62.7, 80.2, 126.9, 128.1, 128.4, 140.2, 175.0. IR (neat): 3325, 1724, 1150 cm$^{-1}$. EIMS m/z: 275(M$^+$), 218(M-t-Bu), 184(M-Bn). HRMS(m/z): M$^+$ C$_{17}$H$_{25}$NO$_2$: Calculated: 275.1885. Found: 275.1893.

EXAMPLE 10

Methyl 3-(benzylamino)butanoate

Synthesis in the same manner as in Example 1(1) using methyl trans-2-butenoate instead of tert-butyl cinnamate and purification by silica gel column chromatography (ethyl acetate/hexane=1/5) gave the title compound (176 mg, yield 85%) as a colorless oil of [α]$^{25}_D$+15.3 (c 0.70, CHCl$_3$).

82% ee (HPLC, Daicel Chiralpak OD-H, hexane/isopropanol=100/1, 1.0 mL/min, 254 nm, major 16.0 min and minor 12.6 min). $^1$H-NMR (500 MHz, CDCl$_3$)δ: 1.16(3H, d, J=6.1 Hz), 1.67(1H, brs), 2.39(1H, dd, J=6.1, 15.3 Hz), 2.50(1H, dd, J=7.0, 15.3 Hz), 3.16(1H, ddq, J=6.1, 6.1, 7.0 Hz), 3.67(3H, s), 3.76 and 3.83(each 1H, d, J=13.2 Hz), 7.22-7.32(5H, m). $^3$C-NMR (125 MHz, CDCl$_3$)δ: 20.4, 41.4, 49.6, 51.2, 51.5, 126.9, 128.1, 128.4, 140.4, 172.7. IR (neat): 3329, 1736, 1176 cm$^{-1}$. EIMS m/z: 208(M$^+$), 193 (M-t-Bu), 134(M-CO$_2$Me).

These are identical to those reported in Asano, N.; Uyehara, T.; and Yamamoto, Y. Tetrahedron 1988, 44, 4173-4180.

According to the present invention, an optically active β-amino acid and a precursor compound thereof can be produced in good yield.

This application is based on a patent application No. 114593/2003 filed in Japan, the contents of which are hereby incorporated by reference.

The references cited herein, including patents and patent applications, are hereby incorporated in their entireties by reference, to the extent that they have been disclosed herein.

What is claimed is:
1. A process for producing an optically active β-amino acid represented by the formula (I)

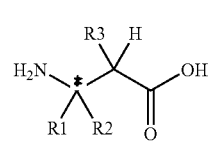

wherein
R1, R2 and R3
are each independently a hydrogen atom, or an optionally substituted alkyl, alkenyl or aryl group, or
R1 and R3 may be linked to form a straight chain or branched chain alkylene having 1 to 4 carbon atoms, provided that R1 and R2 are not the same; and
* shows an asymmetric carbon,
which comprises a step of reacting a compound represented by the formula (II)

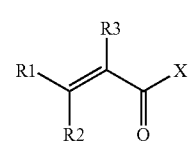

wherein
R1, R2 and R3
are as defined above, and
X is an optionally substituted alkoxy, aryloxy, arylalkyloxy or amino group, with a lithium amide represented by the formula (III)

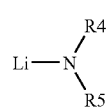

wherein
R4 and R5
are the same or different and each is a silyl-protecting group, or an optionally substituted benzyl, benzhydryl or trityl group,
provided that when one of R4 and R5 is a silyl-protecting group, then the other should be other than a silyl-protecting group,
in the presence of a compound represented by the formula (IV)

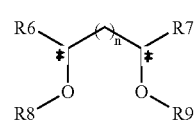

wherein
R6, R7, R8 and R9
are the same or different and each is an optionally substituted alkyl group or aryl group, or R6 and R7 may be linked to form a straight chain or branched chain alkylene having 2 to 5 carbon atoms;
n is an integer of 0 to 3; and
* shows an asymmetric carbon that forms a configuration of (S,S) or (R,R).

2. A process for producing an optically active compound represented by the formula (V)

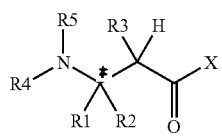

(V)

wherein
R1, R2 and R3
are each independently a hydrogen atom, or an optionally substituted alkyl, alkenyl or aryl group, or
R1 and R3 may be linked to form a straight chain or branched chain alkylene having 1 to 4 carbon atoms, provided that R1 and R2 are not the same;
X is an optionally substituted alkoxy, aryloxy, arylalkyloxy or amino group;
R4 and R5
are the same or different and each is a silyl-protecting group or an optionally substituted benzyl, benzhydryl or trityl group,
provided that when one of R4 and R5 is a silyl-protecting group, then the other should be other than a silyl-protecting group; and
* shows an asymmetric carbon,
which comprises reacting a compound represented by the formula (II)

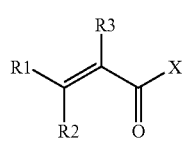

(II)

wherein R1, R2, R3 and X are as defined above, with a lithium amide represented by the formula (III)

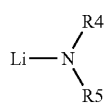

(III)

wherein R4 and R5 are as defined above, in the presence of a compound represented by the formula (IV)

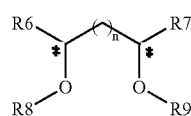

(IV)

wherein
R6, R7, R8 and R9
are the same or different and each is an optionally substituted alkyl or aryl group, or
R6 and R7 may be linked to form a straight chain or branched chain alkylene having 2 to 5 carbon atoms;
n is an integer of 0 to 3; and
* shows an asymmetric carbon that forms a configuration of (S,S) or (R,R).

3. The process of claim 1, wherein the reaction is carried out in the additional presence of chlorotrimethylsilane.

4. A process for producing an optically active β-amino acid represented by the formula (I)

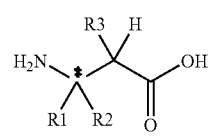

(I)

wherein
R1, R2 and R3
are each independently a hydrogen atom, or an optionally substituted alkyl, alkenyl or aryl group, or
R1 and R3 may be linked to form a straight or branched chain alkylene having 1 to 4 carbon atoms, provided that R1 and R2 are not the same; and
* shows an asymmetric carbon,
which comprises subjecting a compound represented by the formula (V)

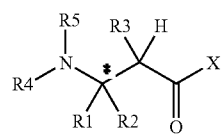

(V)

wherein
R1, R2, R3 and *
are as defined above;
X is an optionally substituted alkoxy, aryloxy, arylalkyloxy or amino group; and
R4 and R5
are the same or different and each is a silyl-protecting group or an optionally
substituted benzyl, benzhydryl or trityl group,
provided that when one of R4 and R5 is a silyl-protecting group, then the other should be other than a silyl-protecting group,
to a deprotection reaction of an amino group and a carboxyl group.

5. A process for producing an optically active compound represented by the formula (VI)

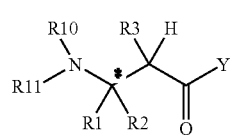

(VI)

19 wherein
R10 and R11
are the same or different and each is a hydrogen atom, or an optionally substituted benzyl, benzhydryl or trityl group,
provided that when one of R10 and R11 is a hydrogen atom, then the other should be other than a hydrogen atom;
Y is a hydroxyl group, or an optionally substituted alkoxy, aryloxy, arylalkyloxy or amino group;
R1, R2 and R3
are each independently a hydrogen atom, or an optionally substituted alkyl, alkenyl or aryl group, or
R1 and R3 may be linked to form a straight or branched chain alkylene having 1 to 4 carbon atoms,
provided that R1 and R2 are not the same; and
* shows an asymmetric carbon,
which comprises subjecting a compound represented by the formula (V)

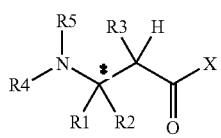
(V)

wherein
R1, R2, R3 and *
are as defined above;
X is an optionally substituted alkoxy, aryloxy, arylalkyloxy or amino group; and
R4 and R5
are the same or different and each is a silyl-protecting group or an optionally substituted benzyl, benzhydryl or trityl group,
provided that when one of R4 and R5 is a silyl-protecting group, then the other should be other than a silyl-protecting group,
to a quenching step.

6. A process for producing an optically active β-amino acid represented by the formula (I)

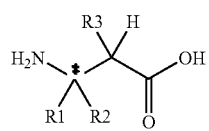
(I)

wherein
R1, R2 and R3
are each independently a hydrogen atom, or an optionally substituted alkyl, alkenyl or aryl group, or
R1 and R3 may be linked to form a straight chain or branched chain alkylene having 1 to 4 carbon atoms,
provided that R1 and R2 are not the same, and
* shows an asymmetric carbon,
which comprises subjecting a compound represented by the formula (VI)

20

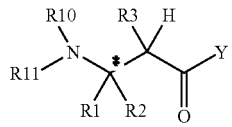
(VI)

wherein
R1, R2, R3 and *
are as defined above;
R10 and R11
are the same or different and each is a hydrogen atom, or an optionally substituted benzyl, benzhydryl or trityl group,
provided that when one of R10 and R11 is a hydrogen atom, then the other should be other than a hydrogen atom; and
Y is a hydroxyl group, or an optionally substituted alkoxy, aryloxy, arylalkyloxy or amino group,
to an amino-deprotecting reaction and, where necessary, a carboxyl-deprotecting reaction.

7. The process of claim 1, wherein R2 is a hydrogen atom.

8. The process of claim 1, wherein R2 and R3 are hydrogen atoms, R4 is a trimethylsilyl group, R5 is a benzyl group, R6 and R7 are phenyl groups, R8 and R9 are methyl groups, n is 0 and X is a tert-butoxy group.

9. The process of claim 8, wherein R1 is a phenyl group.

10. The process of claim 2, wherein the reaction is carried out in the additional presence of chlorotrimethylsilane.

11. The process of claim 2, wherein R2 is a hydrogen atom.

12. The process of claim 2, wherein R2 and R3 are hydrogen atoms, R4 a trimethylsilyl group, R5 is a benzyl group, R6 and R7 are phenyl groups, R8 and R9 are methyl groups, n is 0 and X is a tert-butoxy group.

13. The process of claim 12, wherein R1 is a phenyl group.

14. The process of claim 4, wherein R2 is a hydrogen atom.

15. The process of claim 4, wherein R2 and R3 are hydrogen atoms, R4 is a trimethylsilyl group, R5 is a benzyl group, R6 and R7 phenyl groups, R8 and R9 are methyl groups, n is 0 and x is a tert-butoxy group.

16. The process of claim 15, wherein R1 is a phenyl group.

17. The process of claim 5, wherein R2 is a hydrogen atom.

18. The process of claim 5, wherein R2 and R3 are hydrogen atoms, R4 is a trimethylsilyl group, R5 is a benzyl group, R6 and R7 phenyl groups, R8 and R9 are methyl groups, n is 0 and X is a tert-butoxy group.

19. The process of claim 18, wherein R1 is a phenyl group.

20. The process of claim 6, wherein R2 is a hydrogen atom.

21. The process of claim 6, wherein R2 and R3 are hydrogen atoms, R4 is a trimethylsilyl group, R5 is a benzyl group, R6 and R7 are phenyl groups, R8 and R9 are methyl groups, n is 0 and X is a tert-butoxy group.

22. The process of claim 21, wherein R1 is a phenyl group.

* * * * *